US010201395B2

(12) United States Patent
Döring

(10) Patent No.: US 10,201,395 B2
(45) Date of Patent: Feb. 12, 2019

(54) FILTER MODULE PACKAGING UNIT

(71) Applicant: B. BRAUN AVITUM AG, Melsungen (DE)

(72) Inventor: Stefan Döring, Dresden (DE)

(73) Assignee: B. BRAUN AVITUM AG, Melsungen (DE)

( * ) Notice: Subject to any disclaimer, the term of this patent is extended or adjusted under 35 U.S.C. 154(b) by 155 days.

(21) Appl. No.: 15/417,770

(22) Filed: Jan. 27, 2017

(65) Prior Publication Data

US 2017/0224432 A1 Aug. 10, 2017

(30) Foreign Application Priority Data

Feb. 5, 2016 (DE) .................. 10 2016 102 087

(51) Int. Cl.
| | |
|---|---|
| *B65D 75/36* | (2006.01) |
| *A61B 50/33* | (2016.01) |
| *B65D 75/32* | (2006.01) |
| *B65D 81/26* | (2006.01) |
| *B65D 75/00* | (2006.01) |
| *B65D 77/04* | (2006.01) |
| *A61M 1/14* | (2006.01) |

(52) U.S. Cl.
CPC .............. *A61B 50/33* (2016.02); *A61M 1/14* (2013.01); *B65D 75/002* (2013.01); *B65D 75/326* (2013.01); *B65D 77/0433* (2013.01); *B65D 81/266* (2013.01); *A61M 2209/06* (2013.01)

(58) Field of Classification Search
CPC ........ A61J 1/035; B65D 75/325; B65D 75/36

USPC ........................................... 206/532
See application file for complete search history.

(56) References Cited

U.S. PATENT DOCUMENTS

| | | | |
|---|---|---|---|
| 5,551,557 A * | 9/1996 | Brooks | B65D 81/266 206/204 |
| 5,664,684 A | 9/1997 | Evert | |
| 2005/0063859 A1 | 3/2005 | Masuda et al. | |
| 2016/0015457 A1 | 1/2016 | Hurst | |

(Continued)

FOREIGN PATENT DOCUMENTS

| | | |
|---|---|---|
| DE | 14 86 518 | 5/1969 |
| DE | 10 2007 021 137 | 11/2008 |

(Continued)

OTHER PUBLICATIONS

German Search Report for DE 10 2016 102 087.7 dated Nov. 2, 2016, with translation.

(Continued)

*Primary Examiner* — King M Chu
(74) *Attorney, Agent, or Firm* — RatnerPrestia

(57) ABSTRACT

A sterile filter module/dialyzer packaging including a filter module, preferably a dialyzer, sterile-packaged in a primary packaging. The filter module having an essentially cylindrical central section and a filter module connection formed at the end of the central section. The primary packaging is a blister packaging with a plastic molded part as a lower section forming a receiving compartment for the filter module and a soft upper foil which, with the lower section, closes the receiving compartment for the filter module. The upper foil is fixed onto the lower section so as to be hermetically sealed and the filter module is fixed at least in sections by means of form fit.

18 Claims, 1 Drawing Sheet

(56) References Cited

U.S. PATENT DOCUMENTS

| | | | |
|---|---|---|---|
| 2016/0106149 A1* | 4/2016 | Potter | B65D 81/26 206/265 |
| 2016/0166149 A1* | 6/2016 | Bowers | A61B 5/0006 600/301 |
| 2016/0198990 A1* | 7/2016 | Betancur | A61B 5/150305 206/363 |

FOREIGN PATENT DOCUMENTS

| | | |
|---|---|---|
| DE | 102007036734 A1 | 2/2009 |
| DE | 10 2009 037 107 | 2/2011 |
| JP | H07-291 342 | 11/1995 |

OTHER PUBLICATIONS

European Search Report for Application EP 17154624.5, dated Jun. 14, 2017, 15 pages.

* cited by examiner

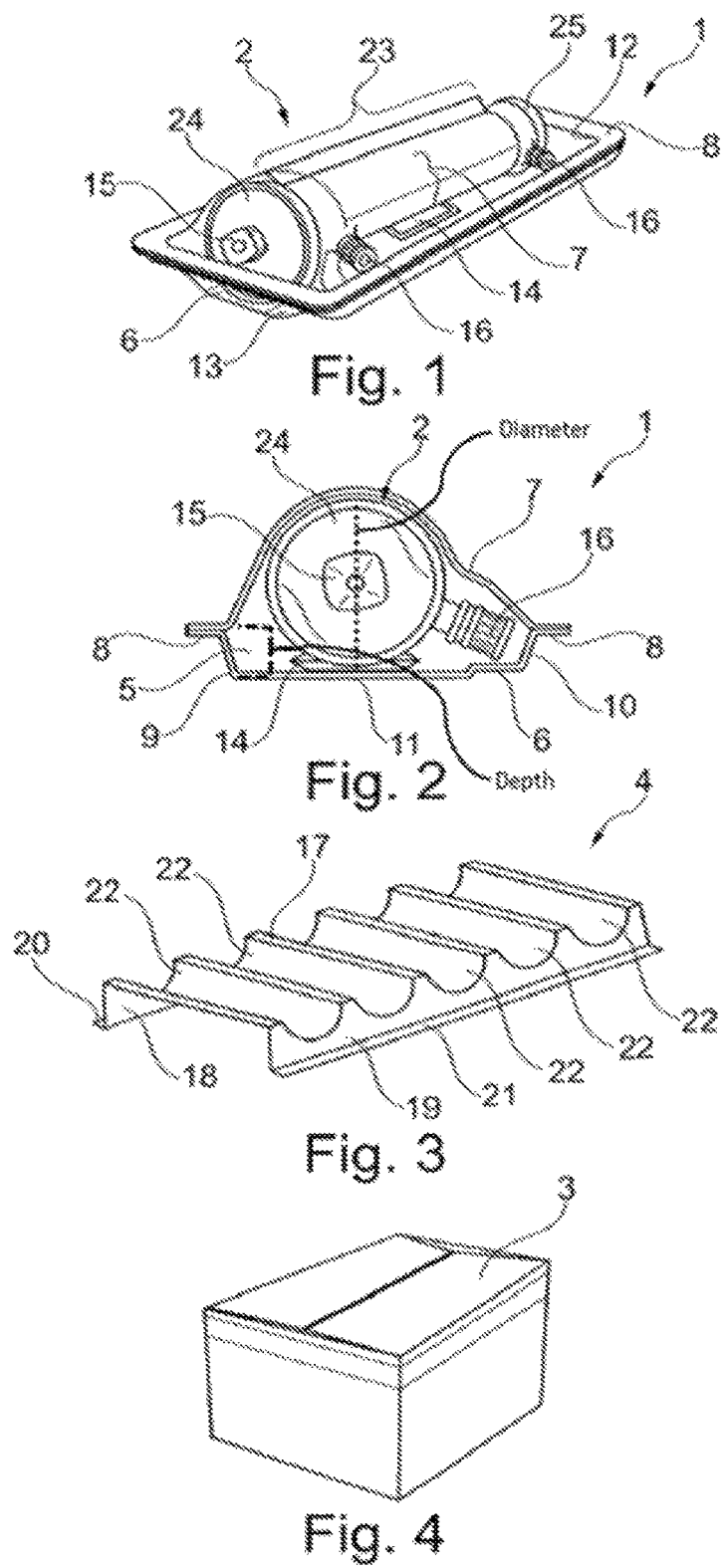

ic application DE 10 2016 102 087.7 filed Feb. 5, 2016, the contents of such application being incorporated by reference herein.

FILTER MODULE PACKAGING UNIT

CROSS REFERENCE TO RELATED APPLICATIONS

This application claims priority to German application DE 10 2016 102 087.7 filed Feb. 5, 2016, the contents of such application being incorporated by reference herein.

FIELD OF THE INVENTION

The invention concerns a sterile filter module/dialyzer packaging unit, comprising a filter module/a dialyzer (filter cartridge, cleaning filter for blood treatment machines etc.) which is sterile-packaged in a primary packaging.

BACKGROUND OF THE INVENTION

In the manufacture of sterile medical products, in particular filter modules/dialyzers, care must be taken to ensure that the product remains sterile until used on a patient or applied as part of a treatment. For this purpose, it must be ensured that either the sterile barrier is applied to the product itself or that the packaging forms a sterile barrier to the environment which remains intact for the shelf-life time shown on the product, assuming realistic storage conditions.

In terms of their external shape, filter modules/dialyzers are designed solely from the point of the demands of production and application technology. Obviously this shape creates particular demands in terms of the packaging of the filter module/dialyzer. An especially problematic feature of the packaging are the standardized, protruding and sharp-edged connectors on the filter module/dialyzer, as well as edges on the filter module/dialyzer and protection caps on the filter module/dialyzer.

Known packagings for medical products, especially for filter modules/dialyzers, primarily consist of a bag made of plastic or aluminium tube or a seal edge bag (as primary packaging), also a tray made of plastic, cardboard or molded pulp and if necessary an external box (as secondary packaging). The tray in particular generally corresponds to the shape of the product packaged in the primary packaging, resulting in a kind of form fit which aims to achieve positionally stable packaging.

Some medical products, in particular filter modules/dialyzers, have to be sterilized in oxygen-free conditions where applicable. This means that at the time of sterilization, the inside of the primary packaging has to be absolutely oxygen-free. This is normally realized by absorption of the oxygen with a suitable medium, a so-called getter. The medium material can be iron powder or a polymer, for example. The absorber can be added to the primary packaging as a so-called sachet or integrated in the structure of the packaging material (foil).

It is a significant disadvantage that the binding of molecular oxygen in the closed system of the primary packaging results in a volume reduction or negative pressure (in an environment which does not change shape). Known packaging systems are not dimensionally stable, so that after closure of the packaging, their volume is uncontrollably reduced to an extent that corresponds to the oxygen binding. Such a volume reduction of primary packaging allows relative movement to occur between the packaged filter modules/dialyzers inside the secondary packaging as well as between the packaged filter modules/dialyzers and the secondary packaging, wherein this relative movement can in turn result in damage to the sterile barrier.

In known filter module/dialyzer packagings, the above-described problem of relative movement as a result of volume reduction in the case of sterilization and the consequential potential damage to the sterile barrier is countered by the use of appropriately thick foils and/or an oxygen-reduced atmosphere during a packaging process. Both methods disadvantageously incur high material and processing costs. Another disadvantage is that volume reductions cannot be entirely ruled out by providing an oxygen-reduced atmosphere in the packaging process, since in this type of packaging, in particular in a filter module/dialyzer packaging, it is necessary to guarantee an atmosphere which is 100% oxygen-free. As a result, the use of an absorber and the resulting volume reductions are unavoidable. Thicker, mechanically resilient packaging materials for the primary packaging increase the product costs while still failing to provide a 100% guarantee that the sterile barrier will not be damaged.

SUMMARY OF THE INVENTION

Based on the above description of the state of the art, an object of the present invention is to eliminate the above-mentioned disadvantages, in particular to provide a sterile filter module/dialyzer packaging unit, with which it is possible to minimize or preferably prevent damage to the sterile barrier resulting from relative movement between packagings as is made possible by uncontrolled volume reduction. The packaging itself should preferably tolerate volume reduction as well as being low-cost and dimensionally stable.

According to aspects of the invention, this object is achieved with a sterile filter module/dialyzer packaging unit, comprising a filter module/a dialyzer sterile-packaged in a primary packaging and with an essentially cylindrical central section and a filter module/dialyzer connection formed at the end of the central section, preferably with a filter module/dialyzer connection formed at each end of the central section wherein the primary packaging is a blister packaging with a plastic molded part forming a receiving compartment for the filter module/the dialyzer as the lower section and an upper foil combined with the latter to form a receiving space for the filter module/dialyzer, wherein the upper foil is fixed onto the lower section so as to be hermetically sealed (welded, bonded, etc.) and the filter module/the dialyzer is fixed at least in sections with form fit, in particular with respect to the lower section or between itself and the lower section. It is also possible to state that the invention provides a hard-soft blister as a (primary) packaging for filter modules/dialyzers. The upper foil of the primary packaging fits tightly (closely) against at least the central section of the filter module/dialyzer. Between the lower section and the upper foil there is therefore only a small amount of air and therefore molecular oxygen, which is advantageous for the sterilization of the filter module/dialyzer packaged in the primary packaging. In the event of sterilization, for example with gamma radiation, for the purpose of which molecular oxygen has to be removed from the closed and sealed packaging, any reduction in volume as a result of sterilization will therefore advantageously be slight as a result.

The packaging of a filter module/dialyzer accounts for a significant portion of its manufacturing costs. With the invention it is possible to advantageously achieve a reduction in costs since the individual components can be especially simply configured yet still ensure sufficient stability of the (primary) packaging in the event of a volume reduction, for example as a result of oxygen absorption. The hard-soft blister packaging (primary packaging) according to aspects of the invention can be particularly simply and effectively adapted or approximated to the shape of the packaged filter module/dialyzer. Relative movement between the filter module/dialyzer and the primary packaging can be reduced to a minimum or even eliminated since the filter module/dialyzer packaged in the primary packaging is securely and soundly fixed with form fit to the upper foil or with form fit to the upper foil and the lower section. Since the packaged filter module/the dialyzer is mainly held by the upper foil, the lower section can be simply configured, thereby enabling simple and low-cost packaging. In addition, this also makes it possible to use a standardized lower section for different filter module/dialyzer sizes with differing diameters. Furthermore, the capacity of the oxygen absorber or getter can be reduced due to the smaller packaging volume, thereby allowing a further reduction in manufacturing costs can be achieved.

According to aspects of the invention, a packaging for filter modules/dialyzers (or other medical products) with a hard-soft blister is used. This is configured in such a way that the filter module/the dialyzer is securely held and fixed in position in the primary packaging. According to one embodiment, this (namely the positioning) can be achieved by defining an area inside the packaging at which the packaging, in particular the molded part, can deform as a result of a volume reduction without impairing the overall stability and basic shape of the packaging. Without impairing the basic shape of the packaging in this sense means that certain external areas of the packaging, with which it rests on other primary packagings or an external packaging for example, are not subject to deformation (creation of predetermined deformation areas). Interior sections of the packaging are likewise essentially resistant to deformation, in particular the molded part with which or on which the dialyzer/filter module is held, positioned or supported.

Preferred embodiments of the invention are claimed in the dependent claims and are explained below.

In order to enable radiation (gamma) sterilization of a filter module/dialyzer packaged in the packaging according to aspects of the invention, one embodiment of the filter module/dialyzer packaging comprises a getter to bind molecular oxygen in the primary packaging, in particular in the receiving space. A volume reduction or a negative pressure arising in the receiving space as a result of the binding of oxygen by the getter does not cause relative movement between individually packaged filter modules/dialyzer modules, since according to aspects of the invention the primary packaging, in particular the upper foil, already fits tightly against the packaged filter module/dialyzer prior to the oxygen absorption. A further volume reduction as a result of the binding of oxygen then particularly advantageously results in an even tighter fitting of the packaging against the filter module/dialyzer. So it is possible to state that the volume decrease as a result of a binding of molecular oxygen, which is normally problematic in packagings according to the state of the art, is advantageously exploited by the invention so as to achieve an even better positioning/attachment of the filter module/dialyzer in the primary packaging. As such, the invention not only successfully suppresses relative movement between filter module/dialyzer (primary) packagings but also holds the packaged filter module/the dialyzer especially effectively in position.

A particular feature of the invention is that the lower section is preferably designed in such a way that it securely holds the filter module/dialyzer. The lower section is preferably configured in the manner of a tray which has a recess for the filter module/dialyzer, the height of which is (significantly) less than the dimensions of the filter module/dialyzer transversely to its axial direction, however. The depth (see FIG. 2) of the receiving compartment for the filter module/dialyzer configured in the lower section is preferably less than half the diameter (see FIG. 2) of the filter module/dialyzer, especially preferably less than a third of the diameter of the filter module/dialyzer, even more preferably less than a quarter of the diameter of the filter module/dialyzer. This is a simple way to ensure that the filter module/dialyzer is largely enveloped and fixed in position by the upper foil. Furthermore, the lower section can be designed in such a way that closing of the filter module/dialyzer connections by the upper foil is prevented or not possible. In the event of radiation (gamma) sterilization, these connections must necessarily remain unobstructed so as to permit movement of oxygen molecules out of the fibre bundle of the filter module/dialyzer. In particular, the upper foil can fit (tightly) against the cylindrical central section of the filter module/dialyzer and not come into contact with the filter module/dialyzer connections formed at each end of the filter module/dialyzer. The upper foil is preferably a shrink foil.

The rigid lower section of the blister combination can exhibit an edge. The upper foil can be sealed on the preferably continuously peripheral edge of the lower section. There can in particular be a form fit between the edge and the external box, thereby limiting or preventing relative movement between the primary packaging and secondary packaging/external box.

The lower section forms a connection receiving structure which is widened with respect to the external contour of the filter module/dialyzer, in particular with respect to the filter module/dialyzer connections, preferably at each end of the central section of the filter module/dialyzer. It is possible for the filter module/dialyzer connections to be held in this receiving structure so that the latter are, advantageously, not closed by either the lower section or the upper foil, while also remaining open in the respective connection receiving structure and fluidically connected to the receiving space, in particular to the connection receiving structure volume.

The advantages of the hard-soft blister according to aspects of the invention come into play in combination with a correspondingly shaped tray in the secondary packaging. In one embodiment of the invention, the filter module/dialyzer packaging unit therefore comprises a tray. This preferably exhibits a holder or receiving compartment for the central section of the filter module/dialyzer enclosed by the upper foil. The tray is preferably configured in such a way that there is a form fit in the axial direction and/or in the tangential direction (of the filter module/dialyzer) with the central section enclosed by the upper foil. It is also possible to state the tray only serves as a holder of the cylindrical section of the filter module/dialyzer, while the geometrically critical areas of the filter module/dialyzer, the so-called "filter module/dialyzer heads", are without contact. The tray is preferably has an essentially U-shaped cross-section. It can in particular exhibit an upper plate and side plates joined to the latter on both sides which act as support legs. In particular, the upper plate can exhibit recesses, preferably partially cylindrical recesses, which run from the one side plate to the side plate on the opposite side, i.e. transversely to the axial direction of the filter module/dialyzer positioned in the primary packaging. One primary packaging with a filter module/dialyzer packaged inside it can be or is inserted in each recess so as to create a form fit with a recess. It is also possible to state that filter modules/dialyzers packaged in the primary packaging are positioned in the cylindrical part of the tray in such a way that the "problem zones" protrude freely and that relative movement is therefore ruled out. The filled trays can be packaged in a conventional external box (secondary packaging).

Furthermore, according to another embodiment, the filter module/dialyzer packaging can comprise an external packaging or secondary packaging in which a number of primary packagings are arranged, each with at least one filter module/dialyzer inserted in it. The external packaging is preferably configured in such a way that between the peripheral edge of the lower section of a primary packaging arranged inside it and the external packaging there is a form fit at least in sections. The tray can be or is preferably inserted so as to create a form fit with the external packaging.

In summary it is possible to state that the fundamental idea on which the invention is based is to use a hard-soft blister for a sterile packaging of a filter module/dialyzer. At least in the cylindrical section of the filter modules/dialyzers according to the above definition, the primary packaging fits tightly against the packaged filter module/dialyzer. A corresponding tray of similar shape fits and supports the filter module/dialyzer in the box exactly at this point, so that structurally sensitive points of the filter module/dialyzer (protection caps and connectors) are uncovered, i.e. do not touch the primary packaging, the secondary packaging or a neighbouring packaging unit. The reduced quantity of air in the (primary) packaging due to the fact that the upper foil fits tightly against the filter module/dialyzer reduces the required absorber capacity in the event of radiation (gamma) sterilization. In addition, the tightly fitting foil limits relative movement between the filter module/dialyzer and the foil and permits a form fit with a corresponding tray. Relative movement between primary packagings and also between primary packagings and the secondary packaging are therefore ruled out, thereby effectively countering any damage to the sterile barrier.

The invention can be used to achieve the following advantages, among others:
- it improves automation (handling), which in particular results in a reduction in manufacturing costs and therefore a reduction in packaging costs,
- it enables a large number of filter modules/dialyzers to be placed in the external box, which in particular results in a reduction in logistics costs,
- it reduces a change in shape as a result of the binding of molecular oxygen in the primary packaging due to the reduced quantity of air in the packaging,
- it provides new design options with straight "communication surfaces" between individual primary packagings and a secondary packaging,
- it limits a range of relative movement which generally results in damage to the packaging and the sterile barriers, due to the upper foil fitting tightly against the filter module/dialyzer
- it reduces the required absorber capacity and
- it increases product security due to clearly recognizable leaks when the upper foil no longer fits tightly against the filter module/dialyzer.

BRIEF DESCRIPTION OF THE DRAWING

The invention is best understood from the following detailed description when read in connection with the accompanying drawing. Included in the drawing are the following figures:

FIG. 1 shows a schematic perspective depiction of a sterile dialyzer primary packaging in a first embodiment;

FIG. 2 shows the dialyzer primary packaging of FIG. 1 in a cross-section running transversely to the axial direction;

FIG. 3 shows a perspective view of a tray for use as part of the invention;

FIG. 4 shows an external packaging for use as part of the invention.

DETAILED DESCRIPTION OF PREFERRED EMBODIMENTS

The term "dialyzer" is mainly used below, wherein at this point attention is drawn to the fact that this can be understood as any type of filter module.

A sterile dialyzer primary packaging 1 (also referred to in the following as primary packaging 1) is shown in FIG. 1 with a dialyzer 2 sterile-packaged inside it. The primary packaging 1 is combined with further primary packagings 1 with dialyzers packaged inside them with a secondary packaging or external packaging/external box 3 and one or more trays 2 to form a packaging unit. The secondary packaging 3 is for example, as shown in FIG. 4, a folding box 3.

According to aspects of the invention, the primary packaging 1 is realized as a hard-soft blister packaging with a lower section 6 which forms a receiving compartment or receiving trough 5 for the dialyzer 2. After proper positioning of the dialyzer 2 inside it, the lower section 6 is hermetically sealed with a lid section 7 placed on top of it in the form of an upper foil 7. The upper foil 7 is a plastic foil, preferably a shrink foil, which is positioned on a peripheral edge 8 of the lower section 6 and hermetically sealed to the latter.

The lower section 6 is made of plastic, for example with moulding, and possesses a defined form with two stable side walls 9, 10 facing each other and a trough 11 positioned between them. The front faces 12, 13 of the lower section together with the side walls 9, 10 and the trough 11 form the receiving compartment 5 for the dialyzer 2 and merge on the latter's open side with the peripheral edge 8. The trough 11, side walls 9, 10 and front faces 12, 13 are configured with the appropriate stability. "Stable" in this sense is taken to mean that the lower section does not essentially deform in the event of negative pressure occurring in the primary packaging due to the binding of oxygen. Unlike the lower section 6, the upper foil exhibits reduced dimensional stability. Reduced dimensional stability in this case means that in the event of negative pressure occurring in the receiving compartment 5 due to a binding of molecular oxygen, it deforms at least in sections and brings about an equalization of pressure. In this event, the upper foil acquires a tighter or closer fit against the dialyzer 2 in a way described later.

In order bind molecular oxygen which, after closing the primary packaging 1, is present in the atmosphere enclosed inside it and in order to remove the molecular oxygen from the atmosphere for the purpose of radiation (gamma) sterilization of the packaged dialyzer, a getter 14 is placed in the receiving compartment 5.

The inner contour of the receiving compartment 5 is configured in such a way that an area of the dialyzer 2 is inserted in it. The stable sides 9, 10, 12, 13 of the receiving space 5 form a volume which is larger than the volume of the sections of the dialyzer 2 inserted in it, so that the latter's radial dialyzer connections 15 and axial dialyzer connections 16 are not closed by the lower section 6 or the upper foil 7 (see in particular FIG. 2). In this way, the inside of the dialyzer 2 is connected fluidically with the atmosphere of the receiving compartment 5 so that molecular oxygen present inside the dialyzer 2 can also be bound with the getter 14. A central cylinder section 23 of the dialyzer 2 between the end dialyzer connections 15, 16 is tightly enclosed by the upper foil 7, see in particular FIG. 2. In his way, the dialyzer 2 is fixed in position and held in the receiving compartment and therefore onto the lower section 6 due to the upper foil 7 fitting tightly against the cylinder section 23 It is also possible to state that the lower section 5 consists of a hard element adapted to the shape of the dialyzer and the soft upper foil 7 tightly envelopes but does not close the dialyzer 2 so that the oxygen absorber 14 can take effect and also bind molecular oxygen from the inside of the dialyzer 2.

FIG. 3 shows the tray 4 which is packaged together with several primary packagings 1 according to FIGS. 1 and 2 in an external packaging 3 according to FIG. 4. The tray 4 has a cross-section running transversely to the axial direction of the dialyzer 2 which is essentially U-shaped. It comprises an upper plate 17 and side plates 18, 19 joined to it which are facing each other. A foot 20, 21 is formed on the side of each side plate 18, 19 facing away from the upper plate 17. A number of recesses 22 are formed in the upper plate 17. These preferably run parallel to each other. As is clearly shown in FIG. 3, they are essentially partially cylindrical in shape, here semi-cylindrical. Each of the recesses 22 forms a receiving compartment for one dialyzer 2 packaged in a primary packaging 1. The primary packaging 1 with the dialyzer 2 hermetically sealed inside it is inserted in the tray 4 in such a way that the upper foil 7 points to the tray 4. There is a form fit between the respective recess 22 and the cylinder section 23 with the upper foil 7 fitting tightly against it. As can be seen in FIG. 1, the two end sections 24, 25 of the dialyzer 2 have a larger diameter than the central cylinder section 23. The width of the tray 4, i.e. the distance between the two side plates 18, 19, is measured such that the respective side plate 18, 19 and the side section 24, 25 of the dialyzer 2 positioned at its side abut each other. The dialyzer 2 packaged in the primary packaging 1 is therefore fixed in position by the respective recess 22 in the tangential direction and by the side plates 18, 19 in the axial direction.

The dimensions of the peripheral edge 8 of the lower section 6 and the external packaging 3 are harmonised in such a way that a number primary packagings 1 can be stably positioned in the external packaging 3.

The invention claimed is:
1. A packaging unit comprising:
    a filter module having an essentially cylindrical central section and at least one filter module connection formed at an end of the essentially cylindrical central section;
    a blister packaging with a plastic molded part as a lower section forming a receiving compartment for the filter module, wherein the lower section is stable and does not deform under an applied negative pressure; and
    an upper foil coupled to the lower section to close the receiving compartment for the filter module, wherein the upper foil is configured to at least partially deform under the applied negative pressure, and wherein the upper foil is fixed onto the lower section to hermetically seal the receiving compartment and is form fit at least in sections to the filter module to fix the filter module position within the packaging unit.
2. The packaging unit of claim 1, wherein the filter module is a dialyzer.
3. The packaging unit of claim 1, wherein the packaging unit further comprises:
    at least one getter positioned within the receiving compartment for the filter module to bind molecular oxygen present in the packaging unit.
4. The packaging unit of claim 3, wherein the getter induces the applied negative pressure by absorption of the molecular oxygen in the packaging unit and wherein the lower section is dimensionally stable so that only the upper foil is deformed as a result of the applied negative pressure.
5. The packaging unit of claim 1, wherein the upper foil fits against the essentially cylindrical central section of the filter module and does not come into contact with the at least one filter module connection formed at the end of the essentially cylindrical central section of the filter module so that they are open.
6. The packaging unit of claim 1, wherein the upper foil is a shrink foil.
7. The packaging unit of claim 1, wherein the upper foil is sealed onto a continuous peripheral edge of the ho-lower section.
8. The packaging unit of claim 1, wherein a depth of the receiving compartment for the filter module in the lower section is less than a diameter of the essentially cylindrical central section of the filter module.
9. The packaging unit of claim 8, wherein the depth is less than half the diameter.
10. The packaging unit of claim 9, wherein the depth is less than a third of the diameter.
11. The packaging unit of claim 10, wherein the depth is less than a quarter of the diameter.
12. Packaging for filter modules comprising:
    at least one of the packaging units of claim 1; and
    external packaging configured to form fit at least sections of a peripheral edge of the lower section.
13. A packaging unit for a filter module with an essentially cylindrical central section and at least one filter module connection formed at an end of the central section, wherein the packaging unit comprises:
    a blister packaging with a plastic molder part as a lower section forming a receiving compartment for at least a portion of the filter module, wherein the lower section is stable and does not deform under an applied negative pressure, the lower section forms a connection receiving structure at both ends of the essentially cylindrical central section of the filter module, and wherein the connection receiving structure forms a volume lamer than a volume of the at least a portion of the filter module received by the receiving compartment to accommodate the at least one filter module connection such that the at least one filter module connection remains open and fluidly connected with the receiving compartment; and
    an upper foil coupled to the lower section to close the receiving compartment for the filter module, wherein the upper foil is configured to at least partially deform under the applied negative pressure, and wherein the upper foil is fixed onto the lower section to hermetically seal the receiving compartment and is form fit at least in sections to the filter module to fix the filter module position within the packaging unit.
14. A packaging for filter modules comprising:
    at least one packaging unit for a filter module with an essentially cylindrical central section and at least one filter module connection formed at an end of the central section, wherein the at least one packaging unit comprises:
        a blister packaging with a plastic molded art as a lower section forming a receiving compartment for the filter module, wherein the lower section is stable and does not deform under an applied negative pressure; and an upper foil coupled to the lower section to close the receiving compartment for the filter module, wherein the upper foil is configured to at least partially deform under the applied negative pressure, and wherein the upper foil is fixed onto the lower section to hermetically seal the receiving compartment and is form fit at least in sections to the filter module to fix the filter module position within the packaging unit; and a tray including a receiving compartment for each of the at least one of the packaging units, the receiving compartment configured to receive the essentially cylindrical central section of the filter module enclosed by the upper foil.

15. The packaging of claim 14, wherein the tray is configured to form fit with the essentially cylindrical central section enclosed by the upper foil in at least one of an axial direction or a tangential direction.

16. The packaging of claim 14, wherein the tray includes a U-shaped cross-section with an upper plate and two slide plates joined on both sides of the upper plate, wherein the upper plate comprises the receiving compartment, which runs from a first of the two side plates to a second of the two side plates, wherein the receiving compartment is configured for form fit with at least one of the packaging units, with a respective filter module packaged therein.

17. The packaging of claim 16, wherein the receiving compartment is a partially cylindrical recess.

18. The packaging of claim 14, further comprising:
external packaging, wherein the tray is configured to at least partially form fit within the external packaging.

* * * * *